(12) United States Patent
Marano et al.

(10) Patent No.: US 9,480,467 B2
(45) Date of Patent: Nov. 1, 2016

(54) ADHESIVE-BASED VARICOSE VEIN TREATMENT

(71) Applicant: Vascular Insights LLC, Madison, CT (US)

(72) Inventors: John P. Marano, Madison, CT (US); Michael G. Tal, Tel Aviv (IL)

(73) Assignee: Vascular Insights LLC, Quincy, MA (US)

( * ) Notice: Subject to any disclaimer, the term of this patent is extended or adjusted under 35 U.S.C. 154(b) by 82 days.

(21) Appl. No.: 14/365,396

(22) PCT Filed: Dec. 13, 2012

(86) PCT No.: PCT/US2012/069495
§ 371 (c)(1),
(2) Date: Jun. 13, 2014

(87) PCT Pub. No.: WO2013/090563
PCT Pub. Date: Jun. 20, 2013

(65) Prior Publication Data
US 2015/0005742 A1 Jan. 1, 2015

Related U.S. Application Data

(63) Continuation of application No. 13/324,621, filed on Dec. 13, 2011, now abandoned.

(51) Int. Cl.
*A61B 17/00* (2006.01)
*A61B 17/12* (2006.01)

(52) U.S. Cl.
CPC ... *A61B 17/00491* (2013.01); *A61B 17/12031* (2013.01); *A61B 17/12109* (2013.01); *A61B 17/12186* (2013.01); *A61B 17/00008* (2013.01); *A61B 2017/00778* (2013.01); *F04C 2270/0421* (2013.01)

(58) Field of Classification Search
CPC ............... A61B 17/00491; A61B 17/12022; A61B 17/12027; A61B 17/12031; A61B 17/12036; A61B 17/12099; A61B 17/12109; A61B 17/12181; A61B 17/12186; A61B 17/12195; A61B 2017/00504; A61B 2017/00513; A61B 2017/1205
USPC ........ 128/898; 606/159, 167–180, 213, 214; 604/93.01
See application file for complete search history.

(56) References Cited

U.S. PATENT DOCUMENTS

| | | |
|---|---|---|
| 5,893,858 A | 4/1999 | Spitz |
| 7,402,320 B2 | 7/2008 | Mirizzi et al. |
| 7,644,715 B2 | 1/2010 | Hayes et al. |
| 7,862,575 B2 | 1/2011 | Tal |
| 7,967,834 B2 | 6/2011 | Tal et al. |
| 8,029,560 B2 | 10/2011 | Bates et al. |
| 2001/0004700 A1 | 6/2001 | Honeycutt et al. |
| 2005/0055040 A1 | 3/2005 | Tal |
| 2006/0095015 A1 | 5/2006 | Hobbs et al. |
| 2007/0282359 A1 | 12/2007 | Tal |
| 2008/0275432 A1 | 11/2008 | Castro et al. |
| 2009/0018486 A1 | 1/2009 | Goren et al. |
| 2009/0270889 A1 | 10/2009 | Tal et al. |
| 2010/0125276 A1 | 5/2010 | Palermo |
| 2010/0217306 A1 | 8/2010 | Raabe et al. |

(Continued)

*Primary Examiner* — Todd J Scherbel
(74) *Attorney, Agent, or Firm* — Baker & Hostetler LLP

(57) ABSTRACT

An intraluminal member can be used to deliver an adhesive to a vein while causing the vein to spasm, thereby controlling adhesive migration and improving procedure efficacy.

21 Claims, 31 Drawing Sheets

(56) References Cited

U.S. PATENT DOCUMENTS

| | | |
|---|---|---|
| 2010/0217313 A1 | 8/2010 | Raabe et al. |
| 2011/0046543 A1 | 2/2011 | Brandeis |
| 2011/0060277 A1 | 3/2011 | Lilley |
| 2011/0066142 A1 | 3/2011 | Tal et al. |
| 2012/0109191 A1* | 5/2012 | Marano, Jr. ...... A61B 17/00491 606/213 |

* cited by examiner

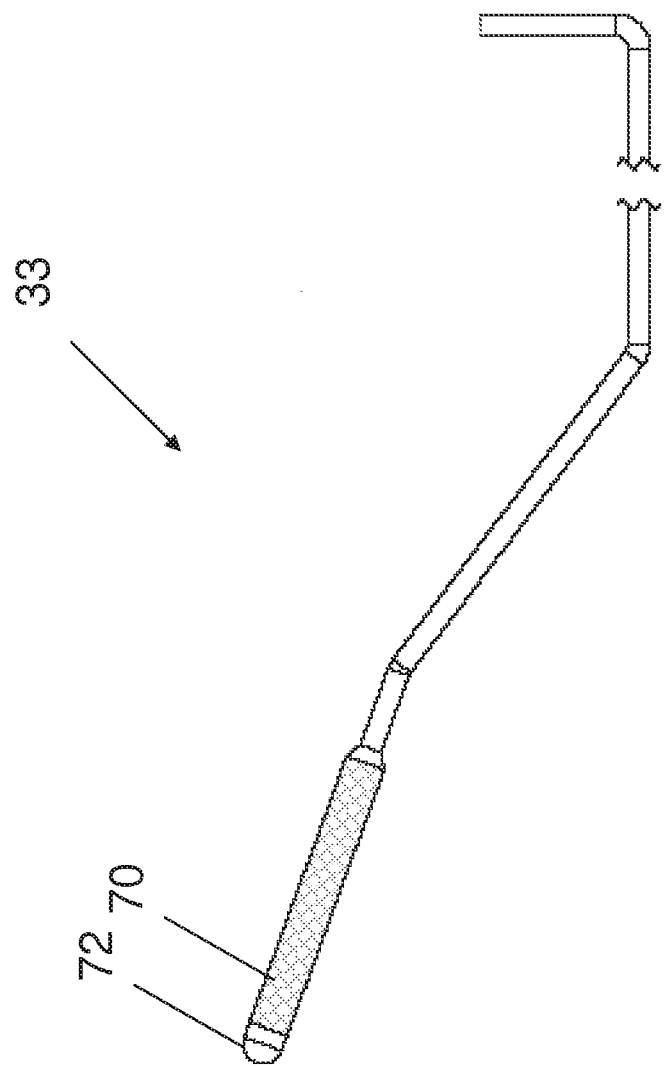

FIG. 14A

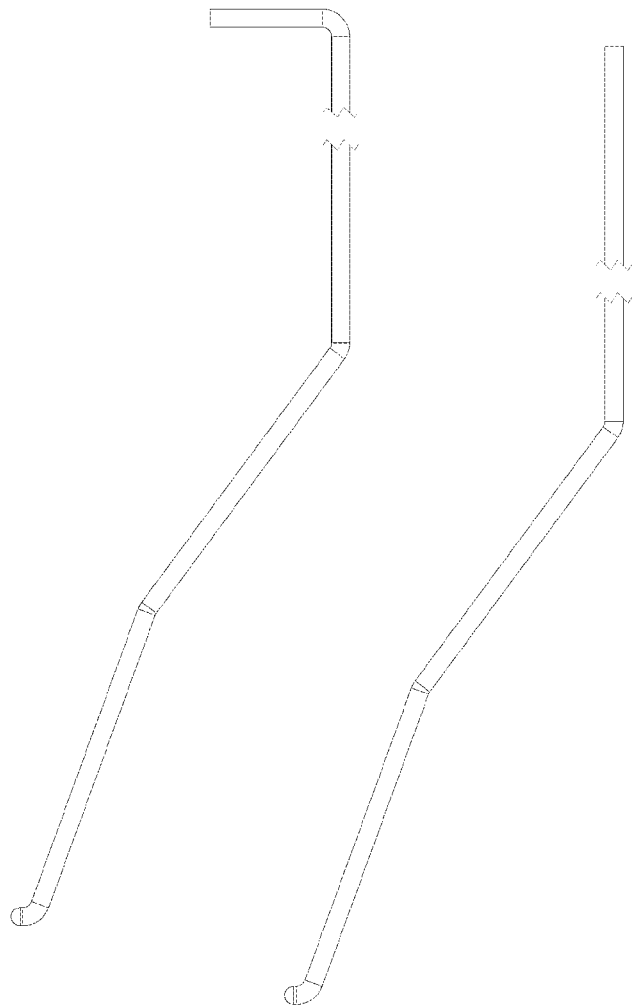
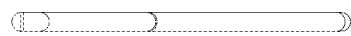
FIG. 15

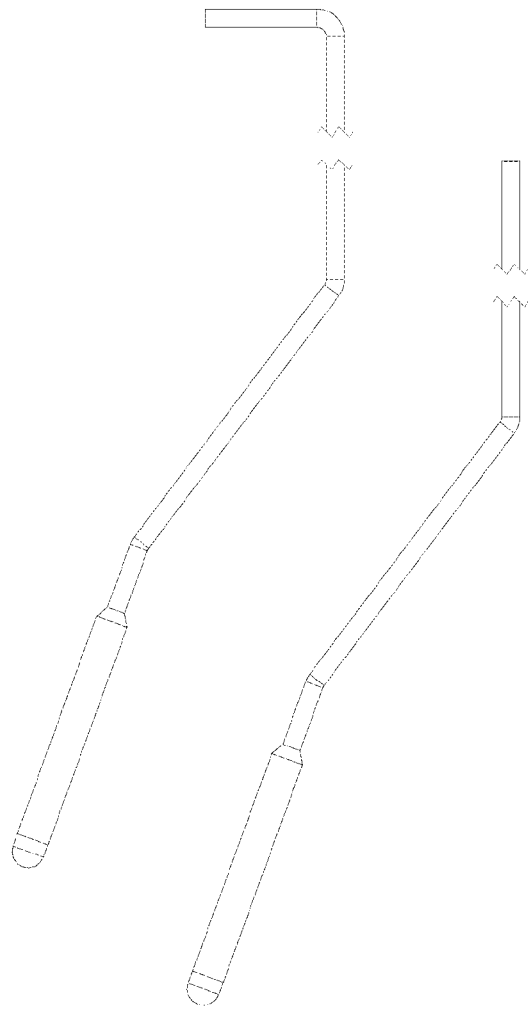
FIG. 17

FIG. 17A

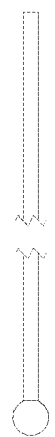
FIG. 18A

FIG. 21A

US 9,480,467 B2

ADHESIVE-BASED VARICOSE VEIN TREATMENT

RELATED APPLICATION

This application claims benefit under 35 U.S.C. 119(e) of U.S. Utility patent application Ser. No. 13/324,621, filed Dec. 13, 2011.

SUMMARY

Conventional adhesive-based varicose vein treatment systems require application of external pressure on the skin overlying the site of injection to compress the vein, reduce the vein diameter and thereby control migration of the adhesive as well as provide approximation of the opposing vein walls to enable effective gluing and occlusion of the vein lumen. Because external pressure can be difficult to apply consistently, and because the consequences of adhesive migration into the deep venous system are potentially so grave, adhesive-based varicose vein treatment may be improved with techniques that achieve reliable and consistent circumferential vein diameter reduction. The present invention is a device that perturbs the inner wall of the vein to induce circumferential vasospasm at or near the site of adhesive injection. Causing spasm at the time of adhesive delivery would provide such finer, more reliable vein diameter reduction and thereby improve control of adhesive migration as well as improve efficacy of the procedure.

BRIEF DESCRIPTION OF THE DRAWINGS

FIGS. 9-10 depict various embodiments of wire distal ends.

FIGS. 14-14A, 15-15A, 16-16A, 17-17A, 18-18A, 19-19A, 20-20A, 21-21A, 22-22A, 23, and 24 depict various embodiments of wire distal ends.

DETAILED DESCRIPTION

Figure 1:
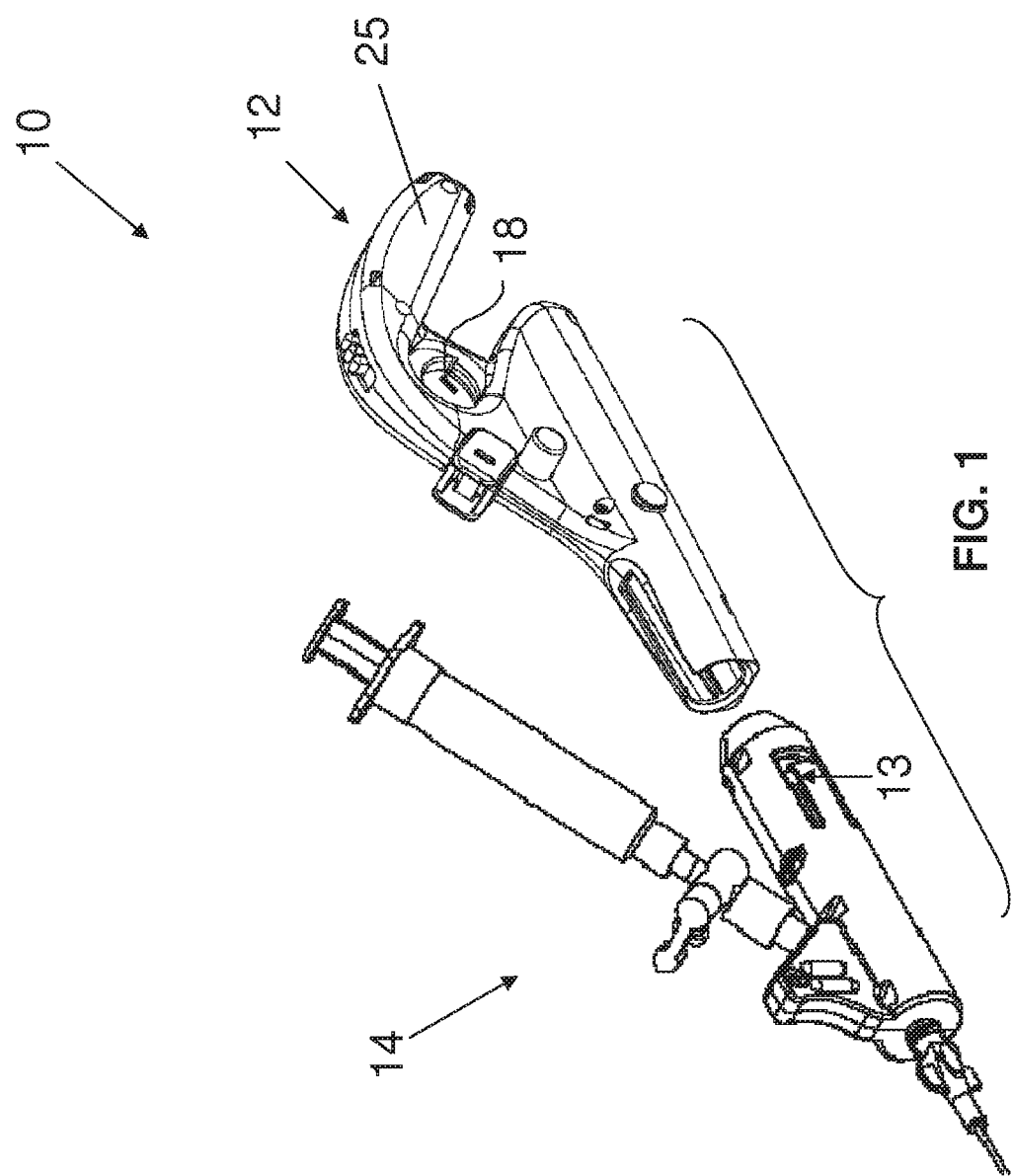
FIG. 1 shows an embodiment of an assembly of a vascular treatment device.
Figure 2:
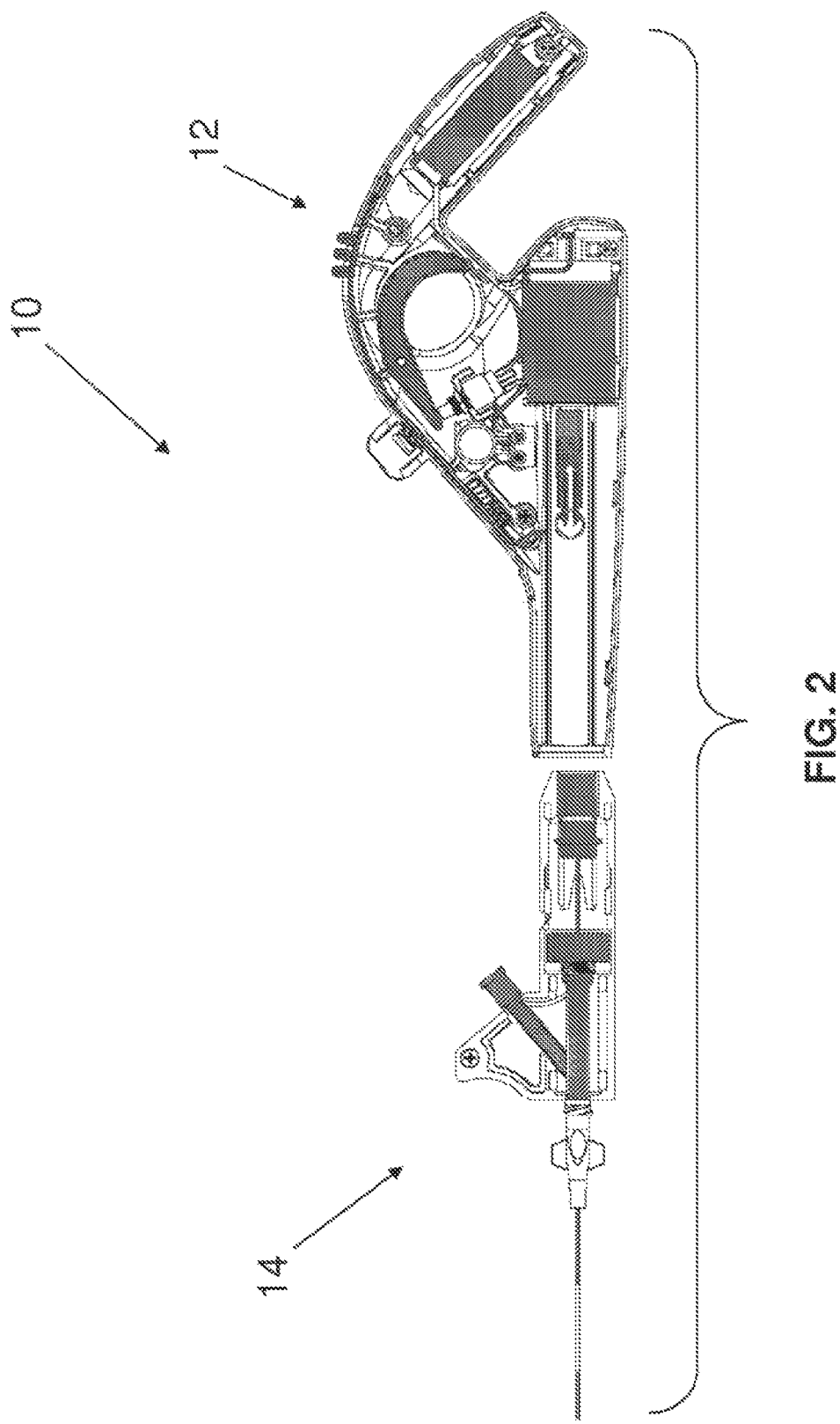
FIG. 2 illustrates a longitudinal cross-sectional view of the embodiment illustrated in FIG. 1.

The ablation of superficial veins that have lost their ability to pump blood to the heart has known beneficial therapeutic effects. The use of adhesives to stop flow in veins, by forming a permanent hardened occluding mass is limited because of concerns of allowing adhesive to enter the deep system. The migration of adhesive into undesirable, otherwise healthy sections can have devastating effects. For example, the use of adhesive to occlude a great saphenous vein, a common vein closure procedure, could result in migration of the adhesive into the deep system, for example, into the common femoral vein. If glue migrates into the deep system it will harden and occlude the deep vein; clot will form proximal and distal to the glue mass and an immovable non-correctable deep vein thrombosis (DVT) will result. The affected extremity will be painful, swollen, and the veins will be engorged. Clot could dislodge and travel to the lungs, causing a pulmonary embolism (PE) associated with a substantial mortality rate). The medical emergency of acute deep vein thrombosis is usually treated by breaking down the clot using thrombolytic agents and anticoagulation (blood thinners). In this case, however, the hardened glue mass is not removable. There is no apparent way to correct the condition. Efforts might be made to surgically bypass the hardened mass but such procedures are known to be risky and have limited success rate. Current procedures to limit the adhesive to the treatment zone and prevent it from inadvertent migration involve adjusting the viscosity of the adhesives to prevent movement, as well as applying external compression by the hand or ultrasound transducer to block passage of the adhesive into undesirable locations. The viscosity approach is quite limiting and complicates both the adhesive delivery system and placement of the agent. External vein compression is unreliable.

The present inventors have discovered that the use of an intraluminal member, such as a rotating (dispersion tip) wire catheter, is an effective, safe approach to deliver an adhesive to veins and arteries while controlling adhesive migration. The rotating dispersion tip in combination with a sclerosant and adhesive or adhesive alone causes vasospasm. The vein consistently and reliably demonstrates circumferential narrowing and a marked reduction in diameter, causing complete occlusion of the treated vein at the treatment site. With spasm, the vein is occluded distal to and at the adhesive injection point, thereby preventing adhesive migration and collateral damage. The spasm blocks adhesive flow to the deep system and also reduces the required volume of adhesive. It provides more effective and reliable vein occlusion. There is no need to block flow to the deep system using external compression or any other methods such as a mechanical plug or balloon. Obstructing flow through spasm caused by the device makes for a safer system.

The use of glue with sclerosant makes the sclerosant procedure safer. An operator can inject sclerosant and adhesive simultaneously, or serially. Either the sclerosant or the adhesive or both can be injected while the rotating wire is perturbing the vein to promote vasospasm. Also, an operator could serially activate the rotating wire device to cause spasm in the target vein, remove the wire, and then inject the sclerosant and/or adhesive into the treatment zone.

Combining the use of adhesive with a rotating wire has the benefit that the spinning tip of the wire will evenly distribute the adhesive radially making the adhesive more effective.

The tip can be configured to cause back flow proximal to the injection point, or the tip configuration may be arranged to provide back flow distal to the injection point to further limit the migration of adhesive into unwanted vein segments. The tip of the device may be positioned at the end of the treatment zone and pulled back or down through the treatment zone. For example, in the great saphenous vein, the tip could be positioned near the sapheno-femoral junction and is pulled away from the junction and through the treatment zone. Because it is highly undesirable (dangerous)

to allow adhesive to enter the deep system (in this example, into the femoral vein), back flow is stimulated in a direction away from the deep system.

Another alternative is to use rotation in a short segment of vein and inject without rotation through the remainder of the treatment zone.

A variety of known adhesives can be used. Usable adhesives can cure in different ways, for example, chemically, or by UV activation. A rotating wire catheter can be configured to deliver UV light at the tip to activate the adhesive. In this manner, adhesive can be delivered through the catheter in a low-viscosity state, which helps minimize the required diameter of the catheter lumen, and then activated when applied or about to be applied. Alternatively, chemically-activated adhesive can be used, with the activator added when the adhesive is applied or about to be applied.

A wide variety of adhesives are suitable for use, principal among them acrylic-based glues, primarily cyanoacrylates, such as 2-octyl-cyanoacrylate (DERMABOND,™ Ethicon) and N-butyl-2-cyanoacrylate (HISTOACRYL,™ B. Braun, Germany; GLUBRAN,™ GEM Srl, Italy; TRUFILL N-BCA,™ Cordis Neurovascular, Inc., US). Other adhesives include BIOGLUE™ surgical adhesive (Cryolife), which is composed of purified bovine serum albumin (BSA) and glutaraldehyde; KRYPTONITE™ adhesive (Doctors Research Group, Inc. of Connecticut.); and fibrin glue. Certain nonadhesive materials, such as the ONYX liquid embolic system (ev3) may also be suitable.

Once adhesive is delivered to the targeted portion of the vein, the adhesive hardens or cures, leaving the vein permanently occluded.

A method of permanently occluding a vein through the combined spasm of the vein and injection of an adhesive can be carried out as follows.

An operator can advance an elongated intraluminal member from an access site and into the vein. The intraluminal member will include a perturbing portion configured to perturb an inner vessel wall of the vein under user control when performing a defined movement. For example, the perturbing portion can be a tip of a rotatable wire and the defined movement can include rotation of the tip, an embodiment explained in more detail below. The defined movement can also include moving the tip longitudinally (i.e., proximally or distally in the vein); the longitudinal movement can be performed simultaneously or serially with rotating. The defined movement can have other effects as well; for example, a wire tip can have a blade configuration similar to a propeller that generates a backflow of blood in the vein when the tip is rotated.

The operator perturbs the vessel wall by performing the defined movement of the perturbing portion of the intraluminal member, thereby inducing a region of the vein to spasm and reduce its diameter.

The operator also injects sufficient adhesive at or near the reduced-diameter region of the vein to occlude the vein permanently. The occlusion may be formed proximal to, distal to, and/or coincident with the reduced-diameter region of the vein. The adhesive may be injected while the defined motion is being performed, or after the defined motion is performed. Sclerosant may also be injected. The sclerosant may be injected simultaneously with the adhesive or serially with the adhesive, at any time in relation to the performance of the defined motion.

The treatment site may be observed during treatment, such as by ultrasound administered by an ultrasound probe placed on the skin overlying the treatment site. Administration of adhesive can be delayed until vein spasm is observed, to help ensure that the adhesive is not introduced into the vasculature until the vein has been prepared to limit adhesive migration.

One example of a rotating wire catheter is described below.

A vascular treatment device may be used for ablating blood vessels, such as varicose veins, and for treating thrombosis by macerating a clot and injecting a thrombolytic drug, among other uses. A vascular treatment device may include a rotatable wire, so sized and shaped for ablating blood vessels, coupled to a cartridge that is engageable to a handle. The wire may thus be indirectly engaged with a motor in the handle such that the wire rotates when the motor is turned on. When the device is used for treating a varicose vein, the rotating wire may perturb the vessel to cause vasospasm, a condition in which blood vessels spasm, and may cause damage to the vessel wall to promote sclerosis.

FIG. 1 shows an embodiment of an assembly of a vascular treatment device 10 having a handle 12 and a cartridge 14. The cartridge 14 may be so sized and shaped to engage to the handle 12 by fitting one component to another as shown. An embodiment of the handle 12 is shown in greater detail in FIG. 3. The handle may define a receptacle 29 in which the male coupling 30 is positioned to receive the female coupling 40 of the cartridge 14 when the cartridge 14 and the handle 12 engage. The handle 12 may include a motor 22, a trigger 26, and a male coupling 30. The male coupling 30 may be connected to the motor 22 in such a way that the motor rotably drives the male coupling upon activation. A potentiometer 24 may be electrically coupled to the motor 22 to control a speed of the motor. The trigger 26 may be mounted on the handle and transitionable between a first state, which does not couple the motor to a power source electrically, and a second state, which couples the motor to a power source.

The handle 12 may also include a power source 20 and a microswitch 28 connected to the motor 22 by a wire 32. The microswitch 28 may be interposed in an electrical circuit connecting the trigger 26 and the motor 22. The microswitch may be biased to an open position such that the circuit between the trigger and the motor is open. When the cartridge 14 is engaged in the handle 12, the cartridge may press against the microswitch, causing it to transition to a closed state, thereby completing the electrical circuit connecting the trigger 26 and motor 22. For example, the microswitch may include two contacts with a conductor that is attached to one contact and disconnected from the second contact when the microswitch is in an open state. In one embodiment, the conductor may include a strip of metal that hangs in the channel into which the cartridge is slid during engagement with the handle. As the cartridge is engaged in the handle, it pushes the metal strip out of the channel and into connection with the second contact of the microswitch. One advantage gained from such configuration may be that a user will not be able to activate the device inadvertently by pressing on the trigger before he/she is ready to use the device, i.e., before the cartridge 14 is fully engaged to the handle 12.

Figure 3:
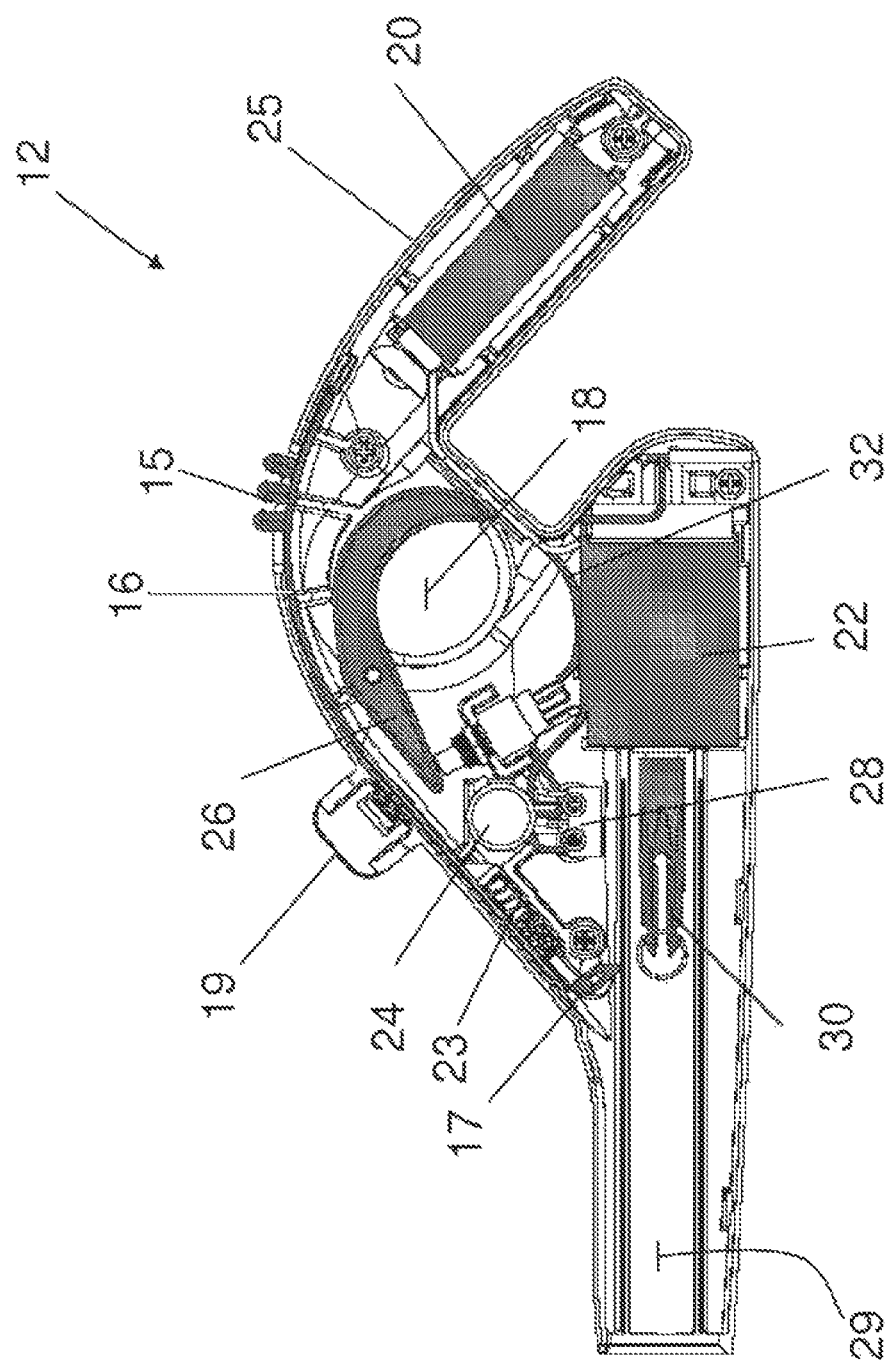
FIG. 3 shows a longitudinal cross-sectional view of a handle.

The handle may 12 also include a switch 16 as shown in FIG. 3. The switch 16 allows the cartridge 14 to be received by, and secured in, the handle 12. The switch may include a grip 15 to permit a user to operate the switch with a finger. The switch may also include a gate 17 that alternately obstructs or locks the cartridge, depending on the gate's position. For example, a user may put a thumb on the grip 15 and push the switch 16 away from the handle grip 25 to transition the switch 16 from a first position, in which gate 17 is positioned in the channel and so prevents engagement of the cartridge 12 and the handle 14, to a second position in which gate 17 is moved out of the channel and thereby permits engagement of the cartridge and the handle. Upon release of the biased switch 16, the gate 17 may fit into a complementary detent in the cartridge and thereby help keep the cartridge engaged with the handle.

The gate 17 may be biased to the first position by a spring 23 contacting the handle. As the user pushes the switch 16 away from the handle grip 25, the switch 16 will push on the spring, thereby creating a restoring force to urge the switch to its original position once the user releases the switch.

As noted above, the gate 17 may be further transitionable to a third position which prevents disengagement of the cartridge 14 from the handle 12. For example, the gate 17 may be forced into the detent 35 (shown in FIG. 4), defined by the cartridge 14, when the biased switch 16 returns to its original position from the second position to lock the cartridge to the handle.

One or more portions of the handle 12 may define a trigger ring 18 in which the trigger is at least partly disposed and about which the handle is so arranged as to be balanced when supported from only one or more portions of the handle that define the trigger ring. In this manner, a user may balance the handle simply by supporting it with a single finger, such as an index finger, against a portion of the handle that defines the trigger ring 18. As motor 22 may well be the heaviest component in the handle, it can be positioned below the trigger 26 as shown in FIG. 3 to reduce the bending moment applied by the motor 22 on a finger supporting the handle by the trigger ring, thereby reducing fatigue experienced by the user.

The handle 12 may be formed by joining two outer casing pieces together.

Figure 4:
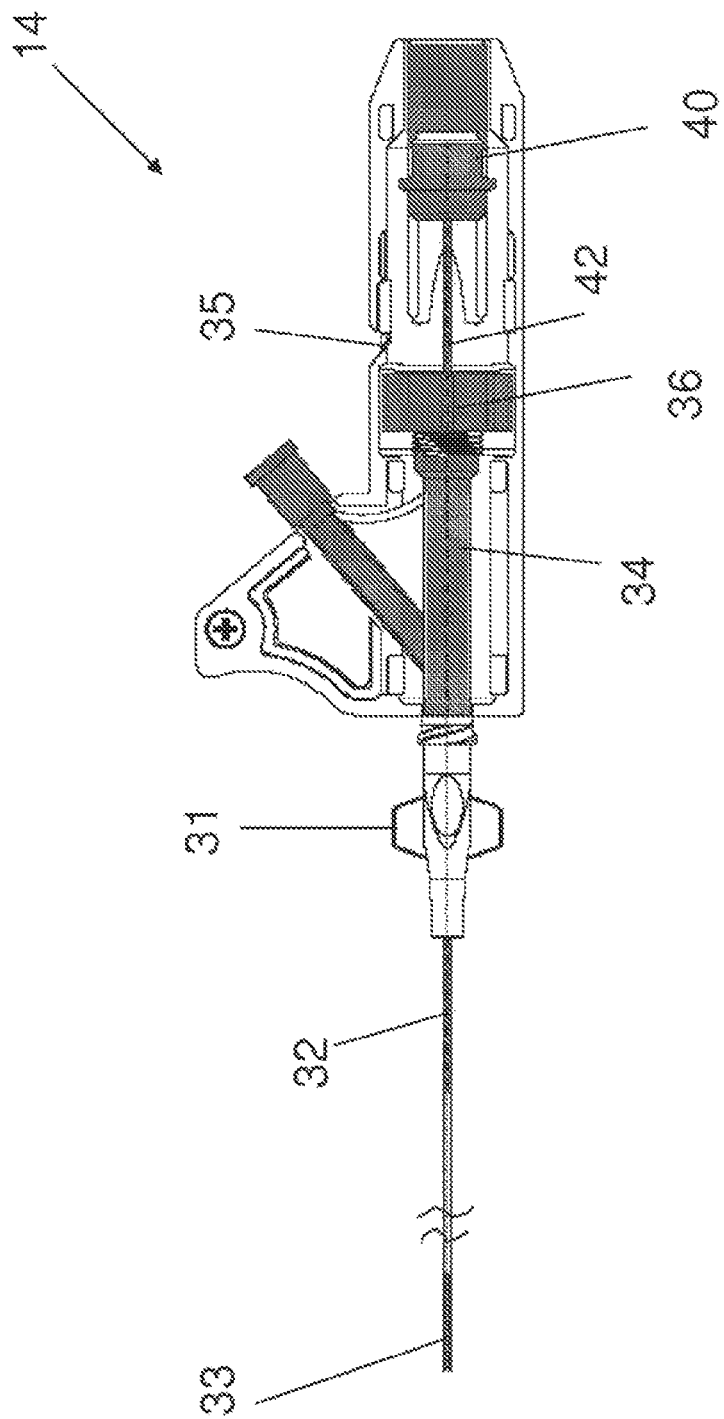
FIG. 4 illustrates a longitudinal cross-sectional view of a cartridge.

An embodiment of the cartridge 14 shown in FIG. 1 is illustrated in greater detail in FIG. 4. The cartridge 14 may include a female coupling 40, a wire 33 (shown as a broken line), and a sheath 32 fixed to and extending from the cartridge 14. The wire may be fixed to the female coupling 40; for example, the wire's proximal tip may be bent approximately 90 degrees to fit through a channel that is sized and shaped to receive the bent end of the wire. A setscrew may be received in the female coupling 40 and/or an appropriate adhesive may be used to secure the wire and prevent it from rotating with respect to the female coupling.

The sheath 32 may define a lumen through which the wire 33 runs. The sheath 32 may have a wide range of inner and outer diameters. In some embodiments, the sheath may have an inner diameter in the range of from 0.022 inches to 0.048 inches. In some embodiments, the sheath 32 may have an outer diameter in the range of from 0.025 inches to 0.051 inches. The outer diameter of the sheath may also be in the range that is consistent with the standard needles having corresponding inner diameters. For example, the sheath may be so sized and shaped to be insertable in a standard needle or vascular sheath having an inner diameter in the range of from 0.0035 inches to 0.1060 inches, or from 0.0160 inches to 0.0420 inches, or from 0.0420 inches to 0.0630 inches, or from 0.0115 inches to 0.0630 inches. The maximum outer diameter of the sheath may be less than 0.035 inches to allow the sheath to be inserted through an intravenous needle or catheter having an inner diameter of less than 0.0039 inches to allow a wider range of practitioners to perform the procedure. Needles, catheters or vascular sheaths with an outer diameter greater than 0.079 inches (6 French, Fr) or 0.092 inches (7 Fr) typically require insertion to be performed by a vascular surgeon or interventional radiologist.

The sheath 32 may also include external markings at regular intervals which may guide the user to monitor the insertion or removal speed of the device 10.

Figure 5:
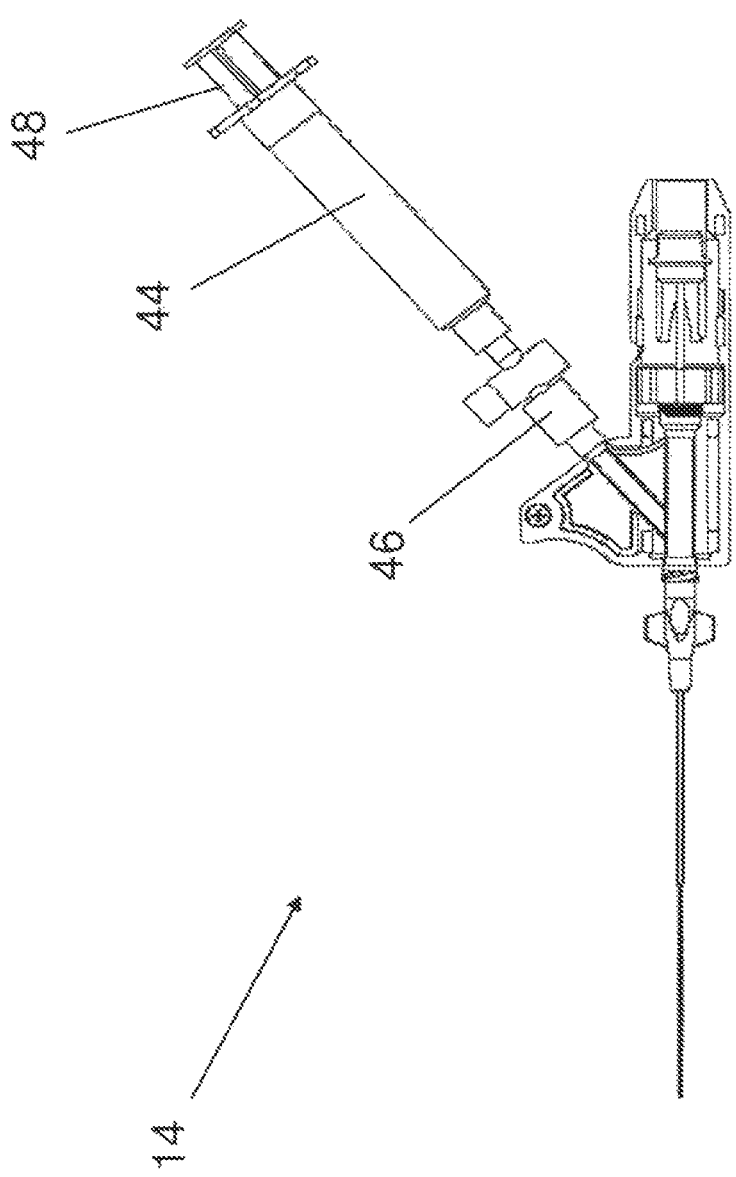
FIG. 5 shows the cartridge illustrated in FIG. 4 with a syringe and a stopcock attached.

One exemplary embodiment depicting a reservoir connectible to the cartridge may include a syringe 44, a stopcock 46, and a plunger 48 as shown in FIG. 5. The syringe 44 may be in fluid communication with the bore of the sheath 32 for releasing a substance at the wire distal end, such as a sclerosant (examples of which include polidocanol, sodium tetradecyl sulfate, and hypertonic saline) and/or adhesive. In this manner, physical perturbation by the wire may be synergistically combined with drug or adhesive treatment to improve device efficacy.

The handle 12 may include a support 19 (shown in FIG. 3) so positioned as to receive the syringe 44. The support 19 may be so sized and shaped to be compatible with the standard syringes and may prevent the syringe from falling out during injection, especially if the material being injected has high volume and/or viscosity and requires significant user thumb pressure upon the syringe. When the cartridge 14 with an attached syringe 44 is engaged to the handle, the syringe 44 may snap onto the support 19. As shown in FIG. 1, the support may be formed from two brackets which cradle the syringe. An alternative embodiment shown in FIGS. 6 and 7 includes a support formed from a single hook that wraps partially around the syringe. These embodiments allow use of the device with the right as well as left hand, depending on the user's preference and/or the patient's position on the treatment table.

The handle 12 and the syringe 44 may be so sized, shaped, and positioned as to permit a user to actuate the trigger 26 with the index finger of a hand and simultaneously depress a plunger 48 into the syringe with the thumb of the same hand, allowing a treatment drug to be deployed from the syringe through the sheath while the wire 33 is rotating. For example, a user may hold the handle by positioning the handle grip 25 in the center of the palm and wrapping third, fourth, and fifth finger around the handle grip and putting an index finger through the trigger ring 18 and if needed, placing a thumb to depress the plunger to release treatment drug into the syringe. The handle may be so designed to allow both right- and left-handed users to operate.

The stopcock 46 shown in FIG. 5 may allow reloading of fluid (such as adhesives and/or sclerosants) and also changing the fluid concentration of composition as well as mixing of fluid with gas. For example, air can be mixed for generating foam as well as agitating an existing mixture and also recreating the foam, because the foam has a limited duration (typically a minute or less) before the fluid and gas start to separate. The stopcock 46 may allow the fluid composition mixture to be agitated without disconnecting the syringe from the cartridge or without stopping the procedure.

A standard Y hemostasis connector 34 as shown in FIG. 4, or other Y hemostasis connector, may be used to aid in fluid communication between the syringe 44 and the lumen defined by the sheath 32. A Y-hemostasis connector 34 may be connected to the female luer hub 31 and to the tubing nut 36 to prevent the fluid from leaking into the region containing the motor 22. An O-ring may be used to prevent leaks around the wire shaft. Wire tubing 42 may be so sized and shaped to receive the wire 33 and attached to the female coupling 40. Combining the above mentioned components may allow the motor to rotate the wire without increasing the torque beyond the appropriate working range. The motor may spin in the range of from 500 to 3000 rpm-4000 rpm for varicose vein destruction and thrombectomy procedures. The handle may also include a built-in RPM display for user to read the speed or may include an electrical port through which the speed may be measured by an external monitor.

The male coupling 30 on the handle 12 may be biased toward an expanded state and transitionable from the expanded state to a contracted state. The female coupling 40 may be so sized and shaped as to transition the male coupling 30 from the expanded state to the contracted state during engagement of the handle 12 and the cartridge 14. As the male coupling 30 and the female coupling 40 fully engage each other, the male coupling displaces the female coupling detents 13 to allow the female coupling to slide within the cartridge.

Attaching the female coupling 40 to the male coupling 30 thereby causes the sheath 32 to slide back relative to the wire. This occurs because the sheath is fixed to the cartridge, while the wire is fixed to the female coupling. As the cartridge is fully seated in the handle, the female coupling is pushed forward in the cartridge. So when the female coupling 40 is not engaged by the male coupling 30, the sheath 32 may cover the distal end of the wire 33, allowing it to be safely advanced in the patient's vasculature; and when the female coupling 40 is engaged by the male coupling 30, the sheath may reveal the distal end of the wire. Consequently, when the female and male couplings are engaged (1) the distal tip of the wire is revealed, and (2) the wire is operably coupled to the motor 22 through the female and male couplings, to allow the motor to rotate the wire 33. As noted above, the cartridge may also trip a lever arm coupled to the microswitch 28 to complete a circuit between the trigger 26 and the motor 22. The male coupling 30 may be so sized and shaped as to return to the expanded state once the cartridge 14 and the handle 12 are fully engaged as described earlier.

The female coupling may be disengaged from the male coupling to re-cover the distal tip of the wire when the wire is to be removed for the site of use, or if a treatment is interrupted. Disengaging the female coupling from the male coupling slides the wire 33 with respect to the sheath 32 (attached to the cartridge fixed to the handle); as a result the tip of the wire is no longer exposed, allowing it to be safely removed. This mechanism may protect the tip of the wire 33 prior to use and also protect the blood vessels and other body tissues during removal or repositioning of the device.

The male coupling 30 may have at least two prongs separated by slitted portions to facilitate the transition from the expanded state to the contracted state. The male coupling may be made with polycarbonate, plastic, or other materials which allow transitioning between an expanded state and a contracted state.

In some embodiments, the vascular treatment device 10 may be of a single piece construct having a handle and a cartridge. The cartridge may be assembled to the handle during manufacturing and be able to transition within the handle between a first position, where the male and female couplings are not engaged, and a second position, where the male and female couplings are engaged. An embodiment of such device may allow the cartridge to slide back and forth within a predetermined range, such as the first and the second position, in the groove defined by the handle, but the cartridge may not disengage itself from the handle. A sheath may be fixed and extend from the cartridge and define a lumen through which the wire runs. The cartridge may also include a syringe to be received by a support mounted on the handle.

In this embodiment, the handle may include a motor, a motor coupling, a trigger, and a power source. The wire having a main shaft, a distal end, and a proximal end which is fixed to the motor coupling may be attached to the motor coupling. The motor coupling may be rotably driven by the motor. The trigger may be mounted on the handle and be transitionable between a first state, which does not couple the motor to a power source electrically, and a second state, which couples the motor to a power source. The handle may also include a microswitch to permit trigger and the motor to be electrically coupled to one another.

At the first position, the cartridge may cover the distal tip of the wire. At the second position, the cartridge (1) exposes the distal tip of the wire from the sheath, and (2) completes a circuit between the trigger and the motor by tripping a lever arm coupled to the microswitch. Therefore, the single piece construct vascular treatment device may allow a user to obtain similar functionality as the device explained earlier and shown in FIG. 1.

Figure 6:
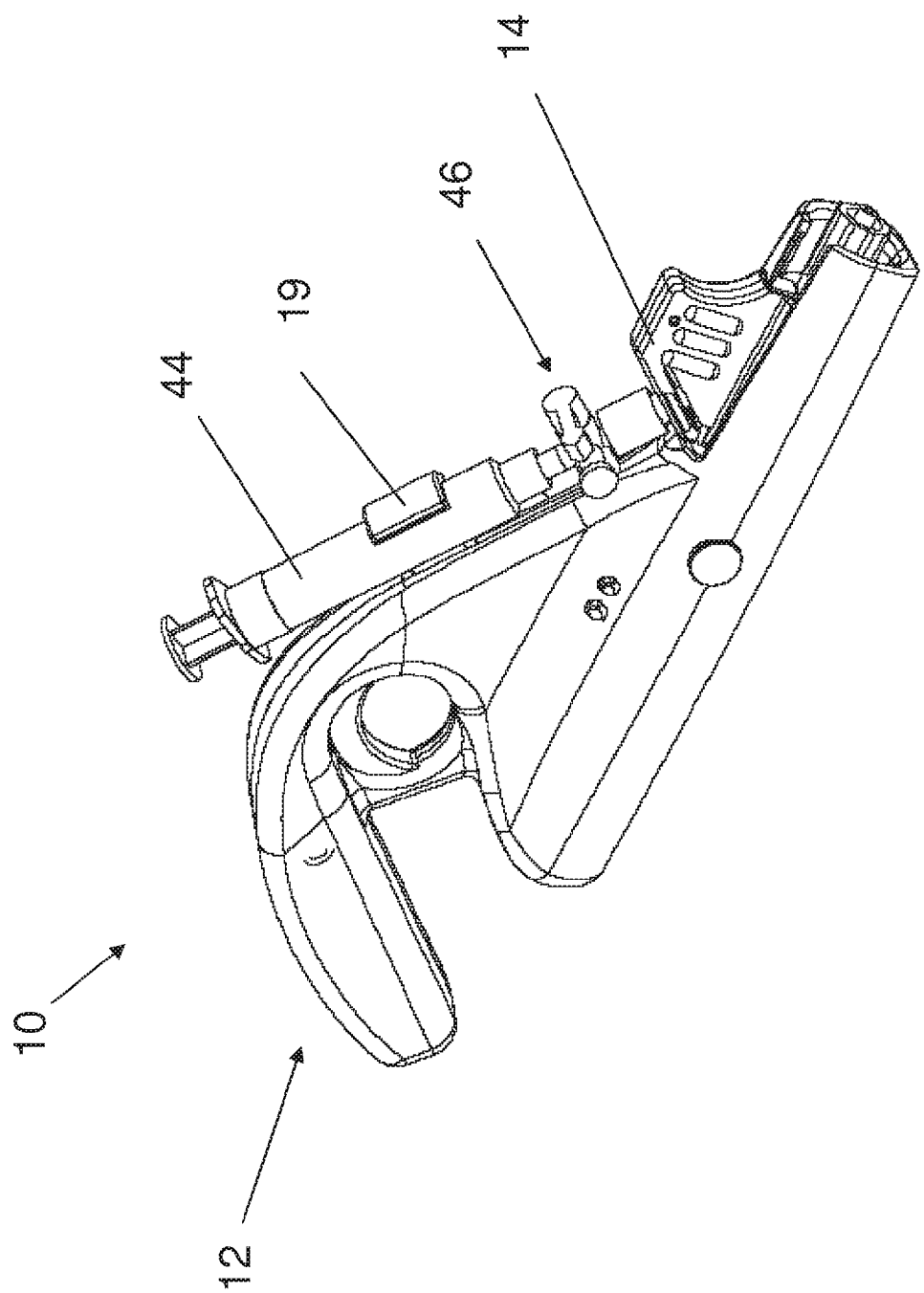
FIG. 6 shows a perspective view of an embodiment of a vascular treatment device having a single syringe support.
Figure 7:
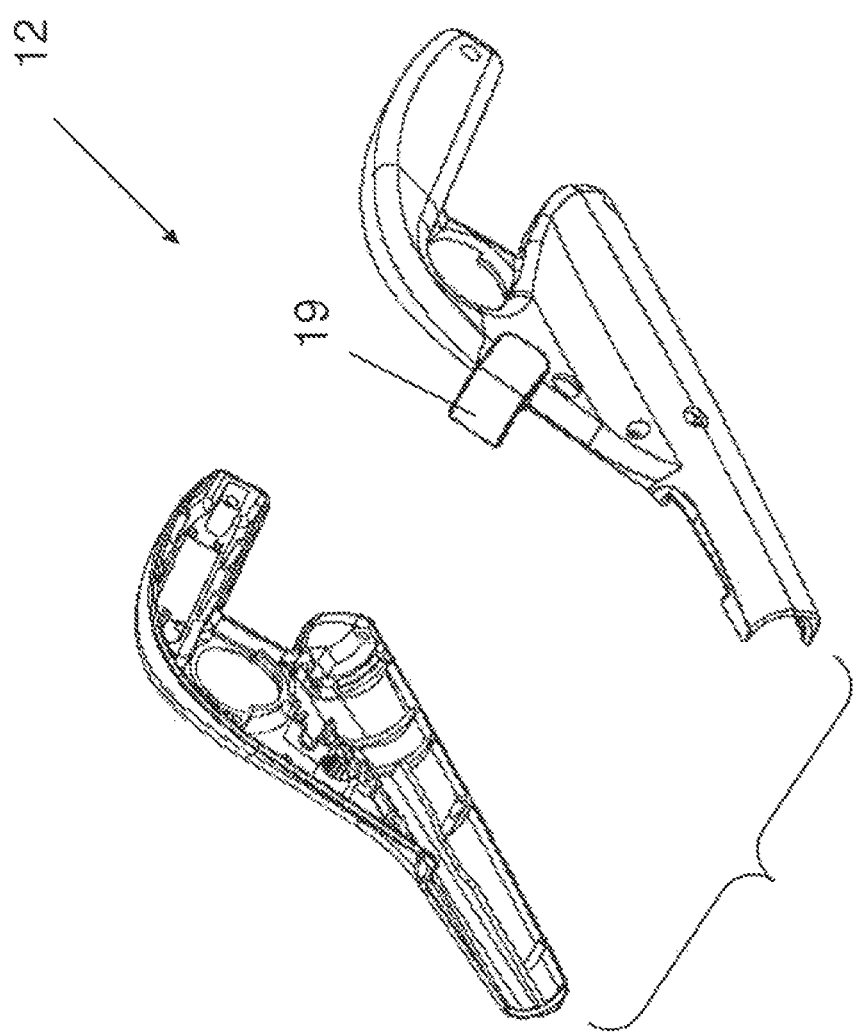
FIG. 7 illustrates an exemplary assembly of the handle of the embodiment depicted in FIG. 5.

FIG. 6 illustrates another embodiment of vascular treatment device 10. The handle may have a support 19 for the syringe 46 in the form of a hook, as described above. This embodiment may be assembled by mating two casings as shown in FIG. 7. The syringe may snap onto the support and remain in position during the use of the device. The support 19 (and/or handle 12) may be made of SLA resin or other materials that would allow the support to withstand the snapping force applied by the syringe.

Figure 8:
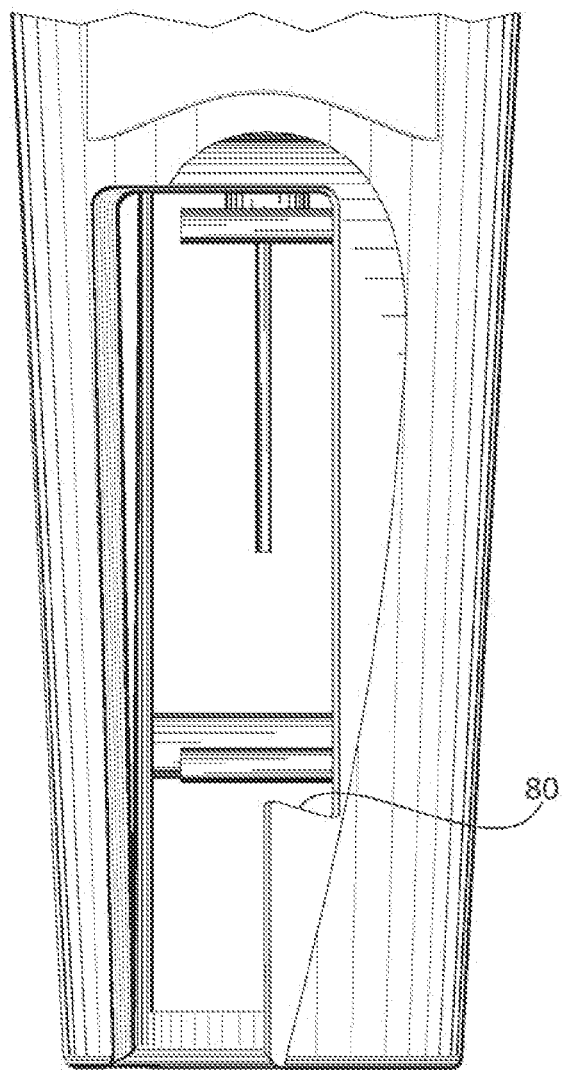
FIG. 8 depicts a top plan view of a portion of the handle illustrated in FIG. 7.

FIG. 8 shows a top view of the end of an alternate embodiment of handle 12 having a notch 80 for retaining the cartridge 14 (not shown) to the handle 12. In the previously mentioned embodiments, the handle had a switch that may be coupled to a gate which held the cartridge to the handle. In this configuration, the notch 80 may prevent the cartridge from disengaging from the handle. In use, a user may slide the cartridge into the handle and then "cock" the cartridge into notch 80 to prevent the cartridge from slipping out of the handle.

A wide variety of distal wire tips may be used; FIGS. 9-11, 14-14A, 15-15A, 16-16A, 17-17A, 18-18A, 19-19A, 20-20A, 21-21A, 22-22A, 23, and 24 show several examples.

Figure 9:
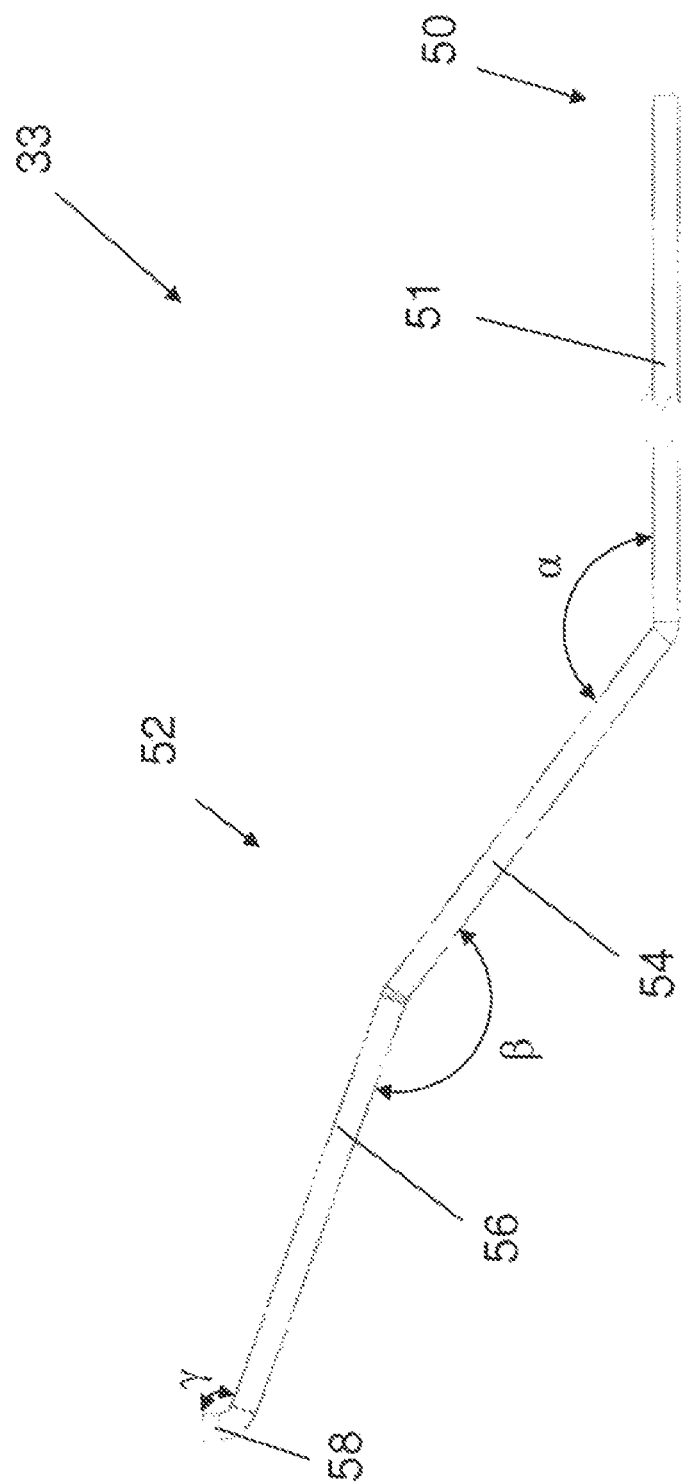

FIG. 9 shows an embodiment of a wire 33 having a proximal end 50, a distal end 52 and in proximal-to-distal order, a first segment 54, a second segment 56, and a third segment 58. The first segment 54 may extend between the main shaft 51 and the second segment 56 and may be biased to a first included angle $\alpha$ that is defined between the main shaft 51 and the first segment 54 and is less than 180 degrees. The second segment 56 may extend between the first segment 54 and the third segment 58 and may be biased to a second included angle $\beta$ that is defined between the first segment 54 and the second segment 56 and is less than 180 degrees. The third segment 58 may extend from the second segment 56 to a free end and may be biased to a third included angle $\gamma$ that is defined between the second segment 56 and the third segment 58 and is less than 180 degrees.

The second included angle may be greater than the first included angle. The sum of the first included angel and the third included angle, minus the second included angle, may be in the range of about 70 degrees to about 110 degrees. The sum of the first included angle and the third included angle, minus the second included angle may be in the range about 80 degrees to about 100 degrees. The sum of the first included angle and the third included angle, minus the second included angle may be about 90 degrees.

The third segment 58 of the wire 33 may have a length that is smaller than the inner diameter of the sheath 32. For example, the third segment 58 may have a length of less than 0.028 inches or it may have a length that is equal to or smaller than two-thirds of the inner diameter of the sheath 32.

The perpendicular distance measured from a center axis of the main shaft 51 to the free end may be less than 0.3 inches. The first segment 54 and the second segment 56 each may have a length in the range of about 0.2 inches to about 0.3 inches, or in the range about 0.24 inches to about 0.26 inches. The length of the first segment 54 may be in the range of about 0.248 inches to about 0.25 inches, and the length of the second segment is in the range of about 0.25 inches to about 0.252 inches. In one embodiment, the length of the first segment 54 may be 0.249 inches, and the length of the second segment is 0.2504 inches.

The distal end 52 of the wire 33 may include at least two linear segments oriented at a non-zero angle relative to one another. Having at least two linear segments may allow the distal tip of the wire to tuck into a sheath without touching the wall of the sheath, and it may also allow the main shaft of the wire to run along the vessel wall while the tip (for example, the third segment) of the wire digs into the vessel wall.

The wire tip located on the distal end 52 may have a wide variety of configurations, depending on the intended use. The wire shape may be "atraumatic," meaning that it may be shaped such that insertion causes little or no spasm or damage to the vessel. For example, FIG. 10 shows a distal end 52 terminating with a hemispheric free end. The hemispheric end may be textured or mechanically or chemically altered to create a roughened surface. Other atraumatic tips may include an end having a full radius, or a J-curved shape, or simply a curved shape.

FIG. 10 shows an atraumatic tip having a sleeve extending from the hemispheric shape along the wire 33 towards the proximal end of the wire. The sleeve 70 can add strength to the distal tip, thereby increasing the scrapping force and increasing the contact surface area to prevent detachment of the hemispheric tip 72.

In other embodiments, the distal tip 52 may be "aggressive" and be bent or curved so that it scrapes the vessel wall. FIG. 9 shows the distal end 52 having a flat free end with a sharp edge around. An aggressive distal tip 52 may also be created by beveling an edge to create a sharp point. The distal tip having a cutting blade, like a shark's fin, may also be aggressive. The distal tip 52 may be roughened to make the distal tip cut more aggressively and/or cause spasm to the blood vessel wall.

A roughened surface may be formed by subjecting an initially smooth steel to abrasion, machining, blasting, chemical etching such as acid etching (for example, nitric acid, hydrofluoric acid, hydrochloric acid, and/or sulfuric acid). A roughened outer surface may also be created by rolling a sheet metal, such as a sheet forming the sleeve 70, onto an irregularly shaped guide to create surface irregularity.

Also, the outer surfaces of the first, the second, and/or the third segments may be coated with an abrasive to roughen the surface. Other surface treatments may include a bastard cut file type or diamond grit. For example, 30 grit diamond may produce an aggressive surface and 200 grit diamond may produce a non-aggressive surface.

During use, especially with a roughened tip, the wire may be periodically re-encased in the sheath to help dislodge debris from the wire tip and keep the device operating normally.

An aggressive surface may also be formed on the first segment 54 and/or the second segments 56 of the wire 33 by introducing a screw threaded profile with a second wire along the length of the wire 33 by following a screw flights of various shapes such as a square, or a rhomboid, or a trapezoid, or a parallelogram, or an ellipse, or a triangle, or a pentagon.

FIG. 10 shows an embodiment having a first segment 56 with a sleeve 70 having a roughened outer surface using one of various methods mentioned earlier. In addition to showing a roughened surface treatment, FIG. 10 further illustrates a wire with a weight added at the distal tip, in this case the weight is added by a sleeve with a roughed outer surface. The weight may be centered on the wire or eccentrically positioned. An eccentric weight may cause the wire to flail about during rotation. The flailing may perturb the vessels more aggressively compared to a wire with centrically added weight.

The distal end 52 of the wire 33 may also include a curved segment. The curvature of the curved segment may be constant, or it may follow other curves, such as a sector of an ellipse or an oval. The distal end 52 of the wire 33 may also have a straight segment distal to the curved segment. Similar to the embodiments with a constant curvature, the curvature of the curved section with a straight segment may be constant or it may follow previously mentioned shapes.

Figure 13:
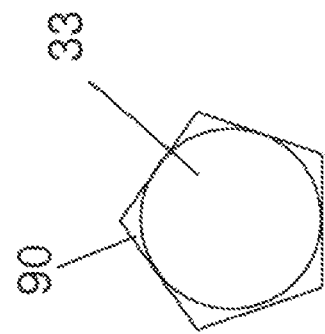
FIGS. 11-13 illustrate transverse cross-sectional views of various embodiments of wire distal tips about which springs are wrapped.
Figure 12:
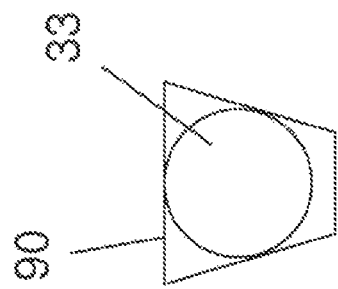
Figure 11:
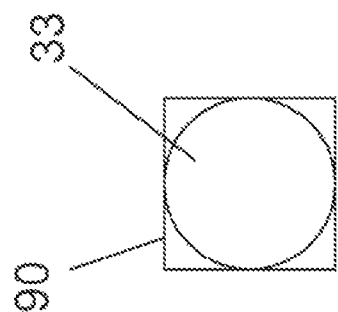

A spring 90 may be attached from the distal end 52 of the wire 33 along the first segment 54 and/or the second segment 56 to create an aggressive cutting surface. The ends of the spring may be brazed at multiple points. The spring 90 may follow the various profiles mentioned earlier. FIGS. 11-13 illustrate cross-sectional views of a spring following screw flights of a square, a trapezoid, and a pentagon, respectively.

The sharp corners of the various profiles (for example, a square, a triangle, a parallelogram, a pentagon) may dig into the blood vessel wall and ablate the vessel wall. The wire 33 may have a hemispheric or a flat free end depending on the intended use. The hemispheric end or flat free end may also be textured or roughened.

Figure 14:
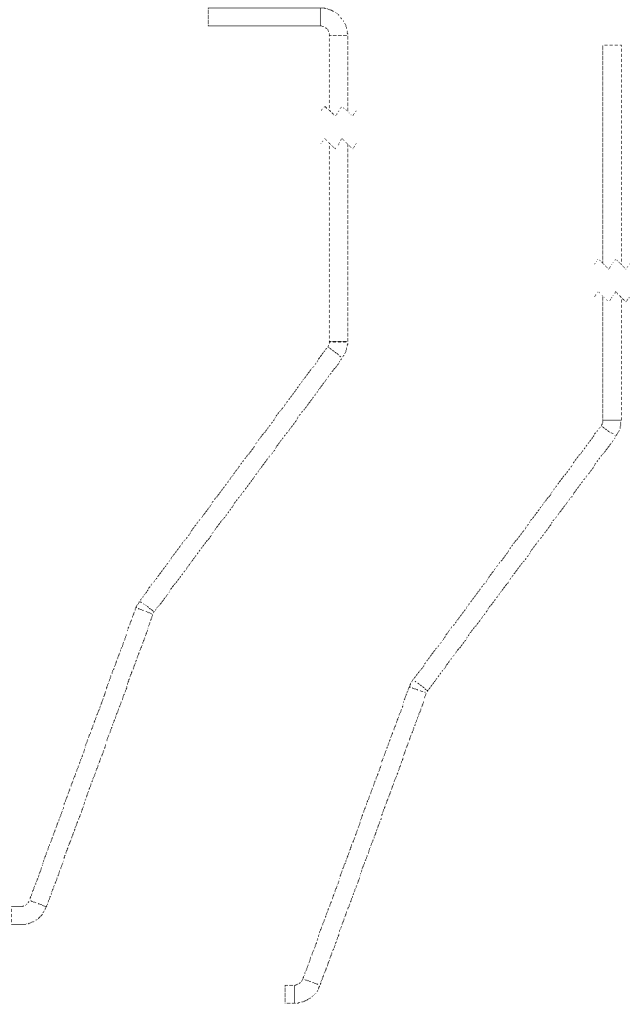

FIGS. 14-14A show a wire similar to that shown in FIG. 9 having first, second, and third linear segments distal to the main shaft.

Figure 15A:

FIGS. 15-15A show a wire similar to that shown in FIGS. 14-14A, in which the free end of the third segment is hemispherical.

Figure 16:
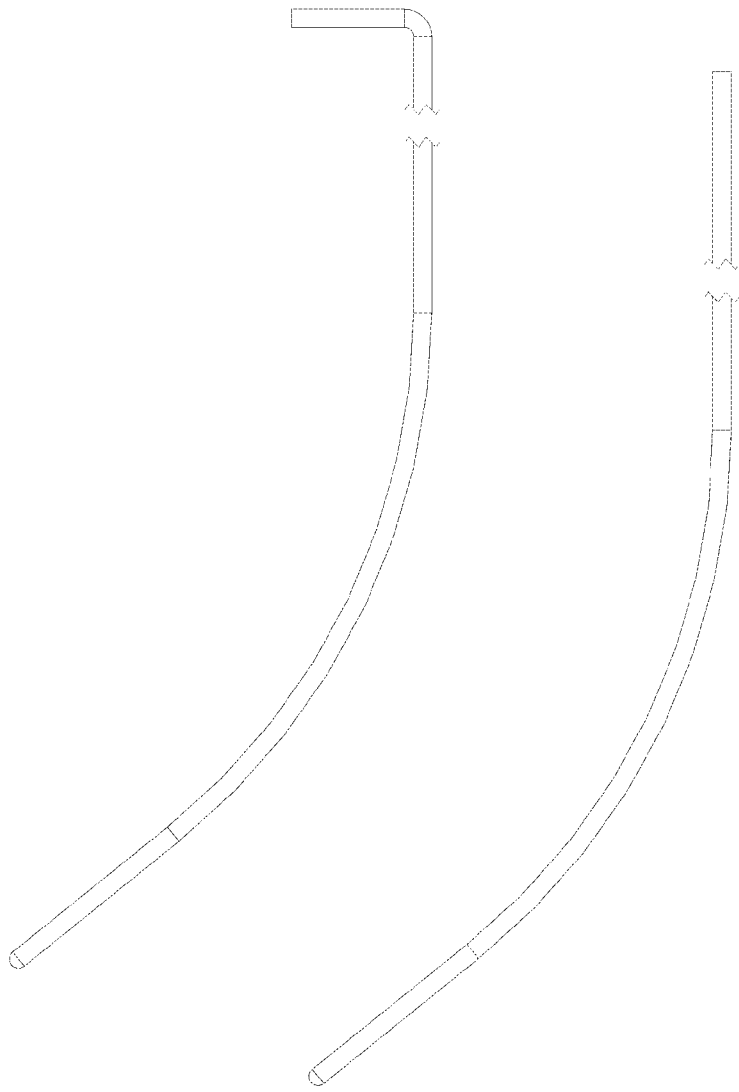
Figure 16A:
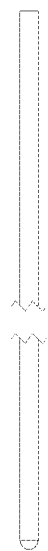

FIGS. 16-16A show a wire having a curved segment distal to the main shaft, and in which the free end of the curved segment is hemispherical.

FIGS. 17-17A show a wire similar to that shown in FIG. 10 having first, second, and third linear segments, with weight added at the distal tip.

Figure 18:
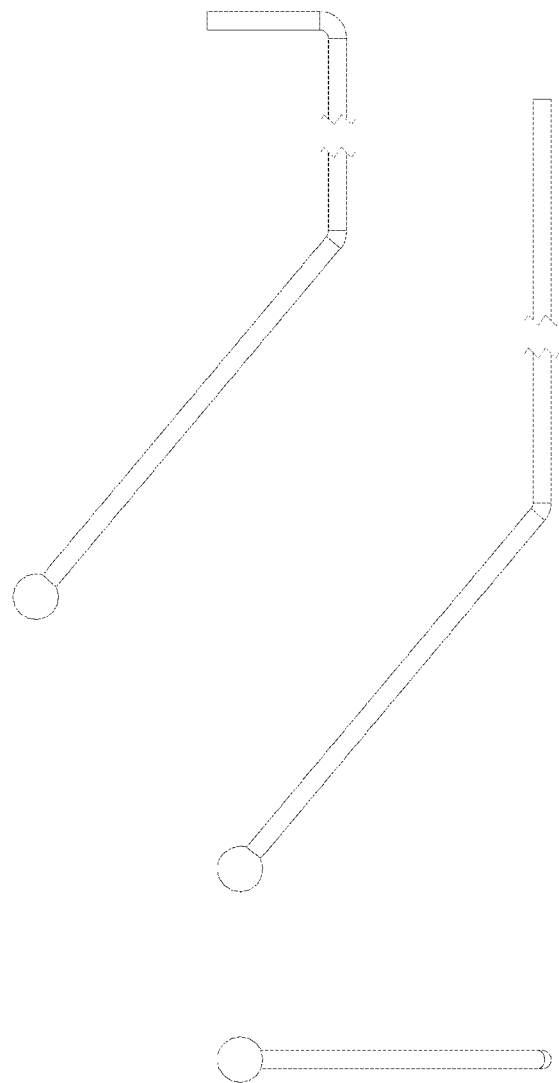

FIGS. 18-18A show a wire having a single linear segment distal to the main shaft, in which the linear segment terminates with a ball-shaped free end.

Figure 19:
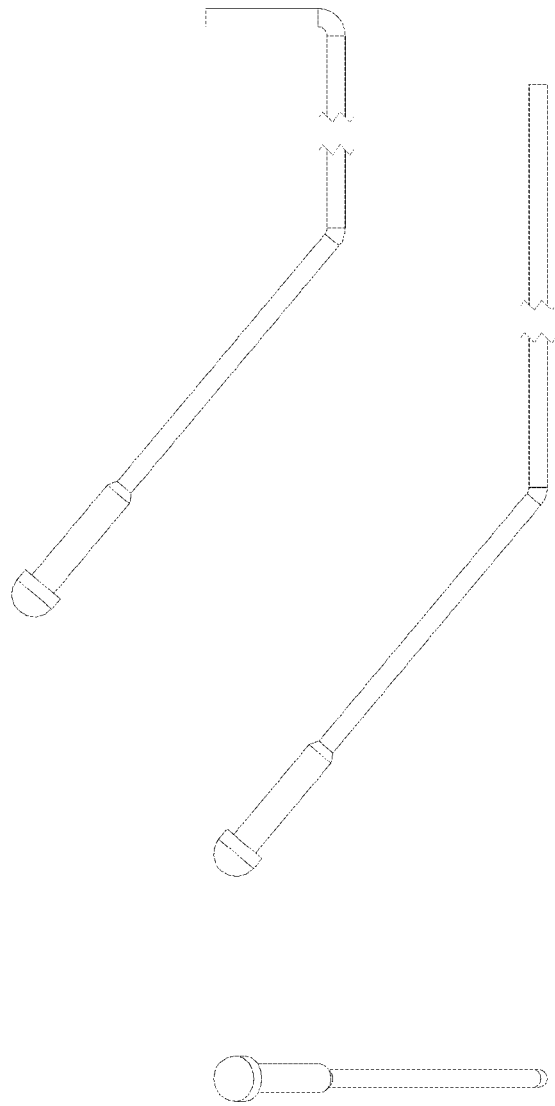
Figure 19A:

FIGS. 19-19A show a wire having a single linear segment distal to the main shaft, in which the distal tip has added weight and the free end is hemispherical.

Figure 20:
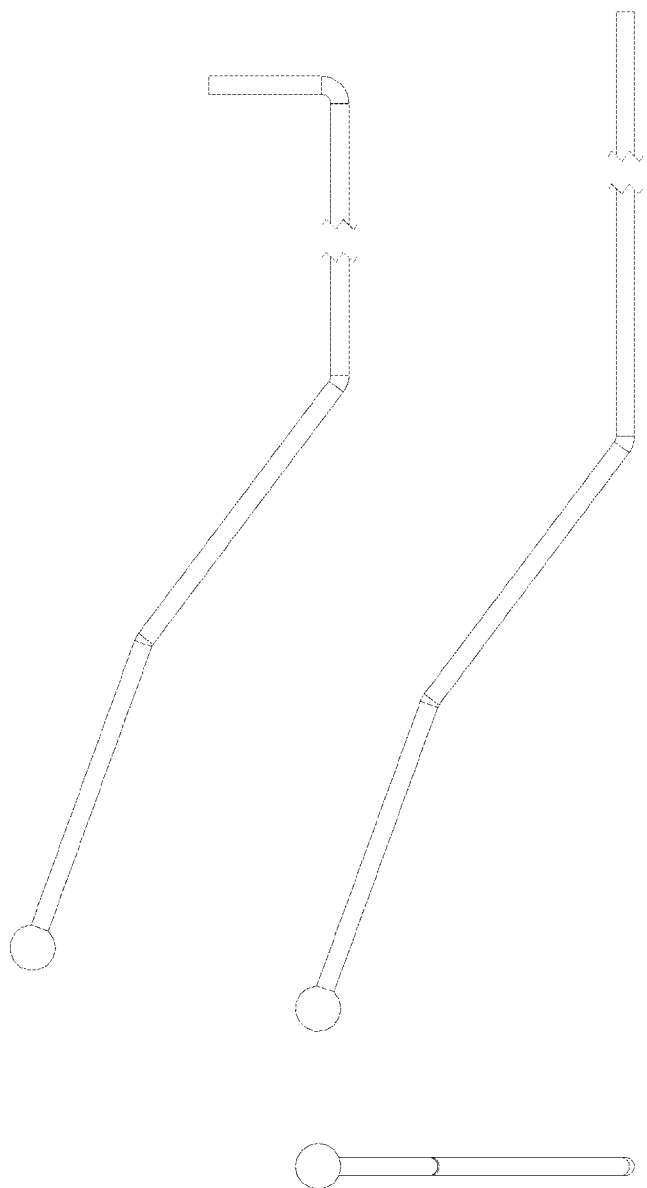
Figure 20A:

FIGS. 20-20A show a wire having two linear segments distal to the main shaft, in which the second linear segment terminates with a ball-shaped free end.

Figure 21:
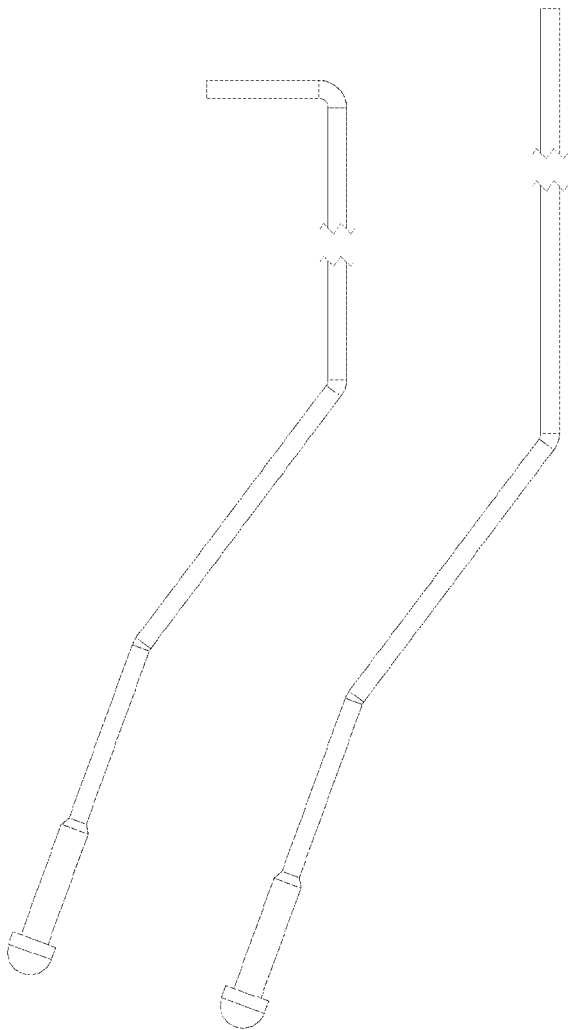

FIGS. 21-21A show a wire having two linear segments distal to the main shaft, in which the second linear segment has added weight and terminates with hemispherical free end.

Figure 22:
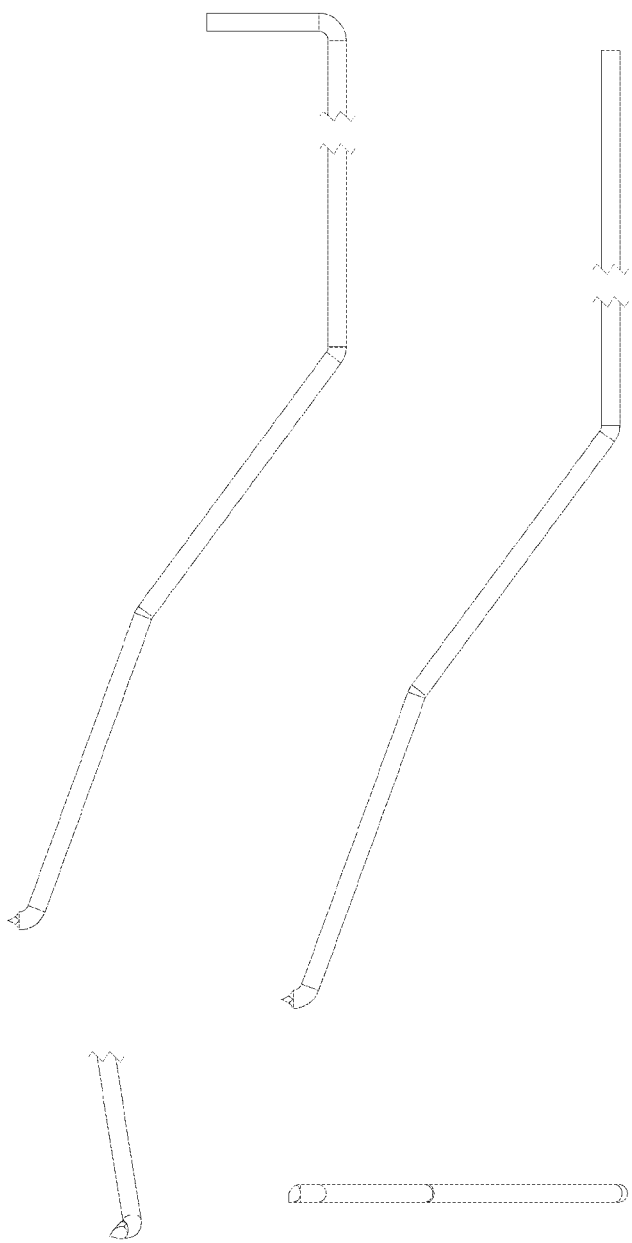
Figure 22A:

FIGS. 22-22A show a wire similar to that shown in FIGS. 14-14A, having three linear segments in which the third segment terminates with a sharp free end.

Figure 23:
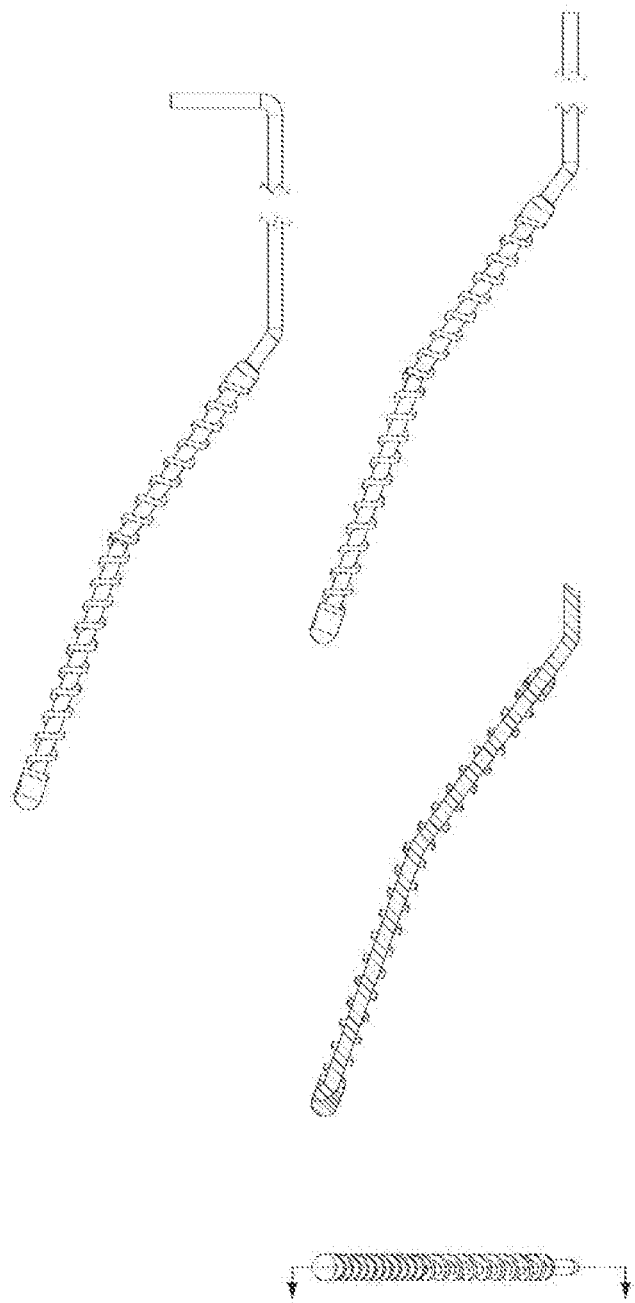
Figure 24:
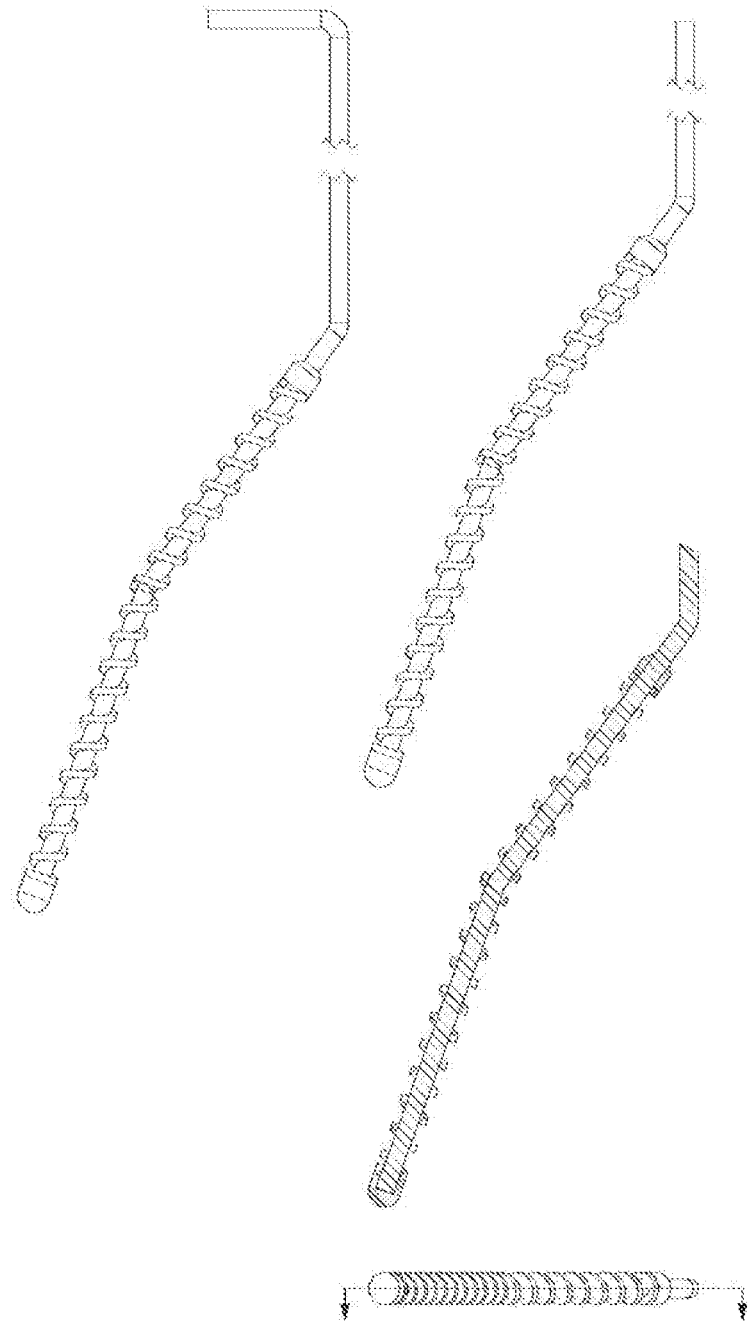

FIGS. 23-24 show wires having a spring wrapped around the distal portion of the wire.

We claim:

1. A method of permanently occluding a vein through the combined spasm of the vein and injection of an adhesive, comprising the following steps:
   advancing an elongated intraluminal member from an access site and into the vein, wherein the intraluminal member comprises a perturbing portion configured to perturb an inner vessel wall of the vein under user control when performing a defined movement;
   perturbing the inner vessel wall by performing the defined movement of the perturbing portion of the intraluminal member, thereby inducing a region of the vein to spasm and reduce its diameter;
   generating backflow of blood in the vein by performing the defined movement, the defined movement includes rotating the perturbing portion of the intraluminal member; and
   injecting sufficient adhesive at the region of the vein having a reduced diameter due to the induced spasm to occlude the vein permanently.

2. The method of claim 1, wherein the perturbing portion is a tip of a wire and the defined movement includes rotating the tip so that the tip contacts the inner vessel wall.

3. The method of claim 2, wherein the defined movement further comprises moving the tip of the wire longitudinally along the vein.

4. The method of claim 3, wherein the tip of the wire is simultaneously rotated and moved longitudinally.

5. The method of claim 2, wherein the wire tip has a blade configuration that generates backflow of blood in the vein when the wire is rotated.

6. The method of claim 1, further comprising injecting sclerosant at or near the reduced-diameter region of the vein.

7. The method of claim 6, wherein the sclerosant and the adhesive are injected simultaneous.

8. The method of claim 1, further comprising observing the treatment site and waiting to inject the adhesive until a reduction in the vein diameter is observed.

9. The method of claim 1, further comprising exposing the adhesive to UV light so as to cure the adhesive.

10. The method of claim 1, further comprising applying external compression on the catheter tip before, during, or after injection of sclerosant.

11. The method of claim 10, wherein the external compression is applied with either (a) an ultrasound probe, or (b) a palm of the operator.

12. The method of claim 1, wherein an outer diameter of the elongated intraluminal member is less than 0.035 inches.

13. A method of permanently occluding a vein through the combined spasm of the vein and injection of an adhesive, comprising the following steps:
   advancing an elongated intraluminal member from an access site and into the vein, wherein the intraluminal member comprises a perturbing portion configured to perturb an inner vessel wall of the vein under user control when performing a defined movement;
   perturbing the inner vessel wall by performing the defined movement of the perturbing portion of the intraluminal member, thereby inducing a region of the vein to spasm and reduce its diameter, wherein the perturbing portion is a tip of a wire and the defined movement includes rotating the tip so that the tip contacts the inner vessel wall, wherein the wire tip generates backflow of blood in the vein when the wire is rotated; and
   injecting sufficient adhesive at or near the reduced-diameter region of the vein to occlude the vein permanently.

14. The method of claim 13, wherein the defined movement further comprises moving the tip of the wire longitudinally along the vein.

15. The method of claim 14, wherein the tip of the wire is simultaneously rotated and moved longitudinally.

16. The method of claim 13, wherein the configuration of the wire tip is a blade configuration.

17. The method of claim 13, further comprising injecting sclerosant at or near the reduced-diameter region of the vein.

18. The method of claim 17, wherein the sclerosant and the adhesive are injected simultaneous.

19. The method of claim 13, further comprising observing the treatment site and waiting to inject the adhesive until a reduction in the vein diameter is observed.

20. The method of claim 13, further comprising exposing the adhesive to UV light so as to cure the adhesive.

21. The method of claim 13, wherein the adhesive is injected in such as manner as to occlude the vein at a location that is either (a) distal to or (b) proximal to the region of spasm.

* * * * *